US00PP08228P

United States Patent [19]

VandenBerg

[11] Patent Number: Plant 8,228

[45] Date of Patent: May 11, 1993

[54] CHRYSANTHEMUM PLANT NAMED BRONZE BRIOSO

[75] Inventor: Cornelis P. VandenBerg, Salinas, Calif.

[73] Assignee: Yoder Brothers, Inc., Barberton, Ohio

[21] Appl. No.: 701,089

[22] Filed: May 16, 1991

[51] Int. Cl.[5] ..... A01H 5/00

[52] U.S. Cl. ..... Plt./82.3

[58] Field of Search ..... Plt./74.1, 82.2, 82.3

[56] References Cited

U.S. PATENT DOCUMENTS

| | | | |
|---|---|---|---|
| P.P. 4,326 | 10/1978 | Shoesmith | Plt. 74 |
| P.P. 4,958 | 11/1982 | Hesse | Plt. 74 |
| P.P. 6,497 | 12/1988 | VandenBerg | Plt. 74 |
| 4,616,099 | 10/1986 | Sparkes | 800/1 |

OTHER PUBLICATIONS

Gosling, ed. 1979. "The Chrysanthemum Manual–6th edition." The National Chrysanthemum Society, London, Essex Telegraph Press, Ltd., pp. 329–336.

Broertjes et al. 1978. "Application of Mutation Breeding Methods in the Improvement of Vegetatively Propagated Crops", Elsevier Sci. Pub. Co., New York, pp. 162–175.

Broertjes et al. 1980. "A mutant of a mutant of a mutant of a . . . Irradiation of progressive radiation–induced mutants in a mutation breeding programme with *Chrysanthemum morifolium*". Euphytica 29:526–530.

Searle et al. 1968. "Chrysanthemums the Year Round". Blanford Press, London, pp. 27–29, 320–327.

Chan. 1966. "Chrysanthemum and rose mutations induced by X-rays", Am. Soc. Hort. Sci. Proc., pp. 613–620.

Broertjes. 1966. "Mutation breeding of chrysanthemums". Euphytica, 15:156–162.

Dowrick et al. 1966. "The induction of mutations in chrysanthem using X- and gamma radiation". Euphytica, 15:204–210.

*Primary Examiner*—Howard J. Locker

*Attorney, Agent, or Firm*—Foley & Lardner

[57] ABSTRACT

A Chrysanthemum plant named Bronze Brioso particularly characterized by its flat capitulum form; daisy capitulum type; greyed-orange ray floret color; diameter across face of capitulum of 108 to 114 mm when fully opened, when grown as a single stem spray cut mum; photoperiodic flowering response to short days of 52 to 67 days; and plant height, with 14 long days after planting rooted cuttings prior to start of short days and with no growth regulator applications, ranges from 107 to 132 cm when grown as a single stem cut mum.

1 Drawing Sheet

The present invention comprises a new and distinct cultivar of Chrysanthemum, botanically known as *Dendranthema grandiflora*, and referred to by the cultivar name Bronze Brioso.

Bronze Brioso, identified as 2837 (83-678B09), is a product of a mutation induction program. The new cultivar was discovered and selected by Cornelis P. VandenBerg in March 1987 in a controlled environment in Salinas, Calif., as one flowering plant within a flowering block established as rooted cuttings from stock plants which had been exposed as unrooted cuttings to an x-ray source of 2000 rads in Fort Myers, Fla., in October 1986. The irradiated parent cultivar was the cultivar identified as Brioso, disclosed in U.S. Plant Pat. No. 6,497.

The irradiation program resulting in Bronze Brioso had as its primary objective the expansion of color ranges of the parent cultivar Brioso. The irradiation program comprised irradiating cuttings of the parent cultivar at irradiation levels of 1500, 1750 and 2000 rads. A total of 593 cuttings harvested from a total of 225 irradiated plants were planted on Feb. 9, Feb. 2 and Jan. 12, 1987, respectively. Of these, 13 initial selections were made, which selections were then revegetated and reflowered. Four consecutive flowerings resulted in discarding 9 of the original 13 selections on Jan. 12, 1988. Three selections were retained as possible introductions, and one selection was retained for possible re-irradiation to obtain a yellow mutation of Brioso, which color was not present in the original selections.

The three retained selections will be commercially introduced as Light Brioso, Dark Brioso and Bronze Brioso. The retained selection for possible re-irradiation yielded a spontaneous yellow mutation, which will be commercially introduced as Yellow Brioso. The other mutations are also disclosed in pending plant applications of applicant.

The first act of asexual reproduction of Bronze Brioso was accomplished when vegetative cuttings were taken from the initial selection in May 1987 in a controlled environment in Salinas, Calif., by technicians working under supervision of Cornelis P. VandenBerg.

Horticultural examination of controlled flowerings of successive plantings has shown that the unique combination of characteristics as herein disclosed for Bronze Brioso are firmly fixed and are retained through successive generations of asexual reproduction.

Bronze Brioso has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Bronze Brioso, which, in combination, distinguish this Chrysanthemum as a new and distinct cultivar:

1. Flat capitulum form.
2. Daisy capitulum type.
3. Greyed-orange ray floret color.
4. Diameter across face of capitulum of 108 to 114 mm when fully opened, when grown as a single stem cut mum.
5. Photoperiodic flowering response to short days of 52 to 67 days.
6. Plant height, with 14 long days after planting rooted cuttings prior to start of short days and with no growth regulator applications, ranges from 107 to 132 cm when grown as a single stem cut mum.

The accompanying photographic drawing is a view of a single stem of Bronze Brioso, with the colors being as nearly true as possible with illustrations of this type.

Of the commercial cultivars known to the inventor, the most similar in comparison to Bronze Brioso is the parent cultivar Brioso. All traits of Bronze Brioso are similar to those of Brioso, except for the ray floret color, and, in several flowering, greater vigor (approximately 5 cm). The ray floret color of Bronze Brioso is greyed-orange, while the ray floret color of Brioso is described as purple. In several flowerings Bronze Brioso had a greater vigor than other Brioso sports, which are mainly distinguished from their parent and from each other by ray floret color. The parent cultivar Brioso was never commercially introduced in Colombia, South America because of low production of flowers per stem, and low night temperature tolerance of the Brioso sports was not evaluated in Colombia.

In the following description color references are made to The Royal Horticultural Society Colour Chart. The color values were determined on plant material grown as a single stem spray cut mum in Salinas, Calif. on Jun. 20, 1990.

Classification:

*Botanical.*—*Dendranthema grandiflora* cv Bronze Brioso.

*Commercial.*—Flat daisy spray cut mum.

INFLORESCENCE

A. Capitulum:
- *Form.*—Flat.
- *Type.*—Daisy.
- *Diameter across face.*—108 to 114 mm when fully opened.

B. Corolla of ray florets:
- *Color (general tonality from a distance of three meters).*—Greyed-orange.
- *Color (upper surface).*—168C to 168D, overlaid and grainy streaked with 168A to 168B.
- *Color (under surface).*—22A to 22B, streaked and overlaid with 168B.
- *Shape.*—Oblong.

C. Corolla of disc florets:
- *Color (mature).*—14A.
- *Color (immature).*—144B.

D. Reproductive organs:
- *Androecium.*—Present on disc florets only; scant pollen.
- *Gynoecium.*—Present on both ray and disc florets.

PLANT

A. General appearance:
- *Height.*—107 to 132 cm when grown as a single stem cut mum with 14 long days after planting rooted cuttings prior to start of short days and no growth regulator applications.

B. Foliage:
- *Color (upper surface).*—147A.
- *Color (under surface).*—147B.
- *Shape.*—Lobed and slightly serrated.

I claim:

1. A new and distinct Chrysanthemum plant named Bronze Brioso, as described and illustrated.

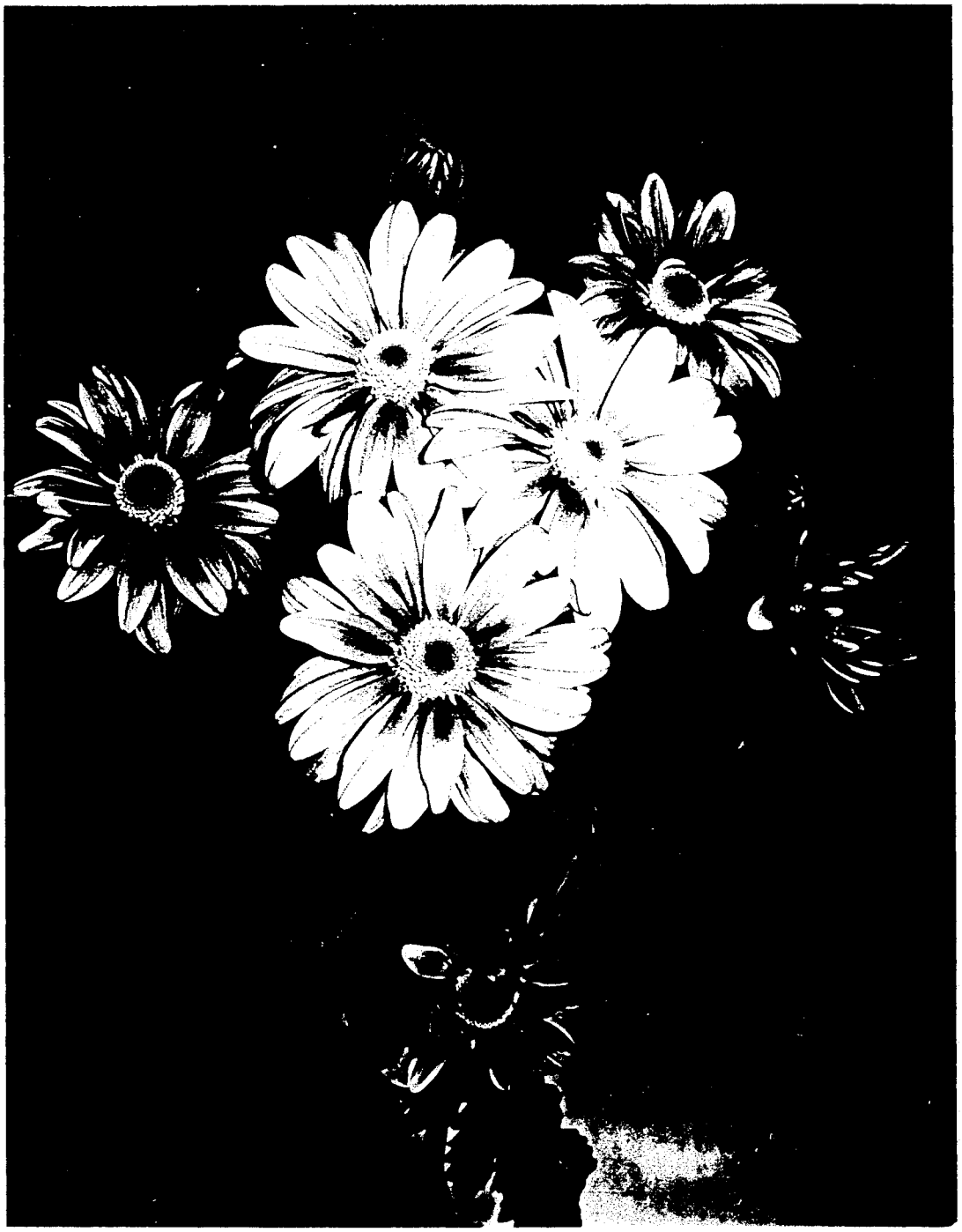

* * * * *